(12) United States Patent
Monfort et al.

(10) Patent No.: US 11,215,600 B2
(45) Date of Patent: Jan. 4, 2022

(54) DEVICE FOR THE IN-LINE MEASUREMENT OF THE PERCENTAGE OF AUSTENITE IN STEELS

(71) Applicant: Centre de Recherches Métallurgiques ASBL—Centrum voor Research in de Metallurgie VZW, Brussels (BE)

(72) Inventors: Guy Monfort, Montegnee (BE); Genevieve Moreas, Wanze (BE); Olivier Herbiet, Plainevaux (BE)

(73) Assignee: CENTRE DE RECHERCHES METALLURGIQUES ASBL—CENTRUM VOOR RESEARCH IN DE METALLURGIE VZW, Brussels (BE)

( * ) Notice: Subject to any disclaimer, the term of this patent is extended or adjusted under 35 U.S.C. 154(b) by 0 days.

(21) Appl. No.: 17/059,295

(22) PCT Filed: Mar. 28, 2019

(86) PCT No.: PCT/EP2019/057867
§ 371 (c)(1),
(2) Date: Feb. 23, 2021

(87) PCT Pub. No.: WO2019/228692
PCT Pub. Date: Dec. 5, 2019

(65) Prior Publication Data
US 2021/0164957 A1 Jun. 3, 2021

(30) Foreign Application Priority Data
Jun. 1, 2018 (BE) .................................. 2018/5364

(51) Int. Cl.
| | |
|---|---|
| *G01N 33/2028* | (2019.01) |
| *C21D 9/56* | (2006.01) |
| *C21D 9/573* | (2006.01) |
| *C21D 11/00* | (2006.01) |
| *G01N 27/72* | (2006.01) |

(52) U.S. Cl.
CPC ......... *G01N 33/2028* (2019.01); *C21D 9/562* (2013.01); *C21D 9/573* (2013.01);
(Continued)

(58) Field of Classification Search
None
See application file for complete search history.

(56) References Cited

U.S. PATENT DOCUMENTS 3,823,368 A * 7/1974 Mansson ............ G01N 27/9046
324/233
3,872,379 A * 3/1975 Brooks .................. G01R 27/00
324/242
(Continued)

FOREIGN PATENT DOCUMENTS

| | | |
|---|---|---|
| JP | H 07190991 A | 7/1995 |
| JP | H 07325067 A | 12/1995 |
| JP | H 0862181 A | 3/1996 |

OTHER PUBLICATIONS

Zhu, W., et al. "Development and Deployment of Online Multifrequency Electromagnetic System to Monitor Steel Hot Transformation on Runout Table of Hot Strip Mill." Ironmaking & Steelmaking, vol. 41, No. 9, 2014, pp. 685-693 (Year: 2014).*
(Continued)

*Primary Examiner* — Paul A Wartalowicz
*Assistant Examiner* — Ryan L Heckman
(74) *Attorney, Agent, or Firm* — Leydig, Voit & Mayer, Ltd.

(57) ABSTRACT

A method for electromagnetic and real-time measurement of a percentage of austenite contained in a steel strip in continuous motion during in-line manufacture or transformation thereof, by a device including the steel strip and a measuring device including at least: an alternating-current generator; a first coil supplied by the alternating-current generator, called a transmitting coil, and a second coil, called
(Continued)

a receiving coil, the first and second coils being arranged parallel to each other or coaxial and on both sides of the steel strip, a distance between the coils being fixed and between 10 and 200 mm; a core of ferromagnetic material being a center of each coil, respectively; and at least one voltage-measuring device connected to terminals of the receiving coil, being a multimeter or an electronic acquisition system having an analog-digital converter coupled to a computer, to obtain the percentage of austenite contained in the steel strip.

19 Claims, 2 Drawing Sheets

(52) U.S. Cl.
CPC .............. *C21D 11/00* (2013.01); *G01N 27/72* (2013.01); *C21D 2211/001* (2013.01)

(56) References Cited

U.S. PATENT DOCUMENTS

| | | | | |
|---|---|---|---|---|
| 4,740,747 | A * | 4/1988 | Kawashima | G01N 27/72 324/203 |
| 5,942,893 | A * | 8/1999 | Terpay | G01P 3/49 324/207.18 |
| 2007/0006651 | A1 * | 1/2007 | Kruger | G01N 29/11 73/579 |
| 2011/0257703 | A1 * | 10/2011 | Kerber | A61N 1/36038 607/57 |
| 2015/0323502 | A1 * | 11/2015 | Suetsugu | G01N 27/9006 324/240 |

OTHER PUBLICATIONS

Yadav, Akash. "Effect of Temperature on Electric Current, Magnets and Electromagnet." International Journal of Advancements in Technology, vol. 07, No. 04, 2016 (Year: 2016).*

García-Martin J, Gómez-Gil J, Vázquez-Sánchez E. Non-destructive techniques based on eddy current testing. Sensors (Basel). 2011;11(3):2525-65 (Year: 2011).*

Lois, et al. "Assessment of Martensite Content in Austenitic Steel Specimens by Eddy Current Testing," *Insight—Non-Destructive Testing and Condition Monitoring* 48, 1:26-29 (Jan. 1, 2006).

Lois A et al.: "Assessment of martensite content in austenitic steel specimens by eddy current testing", Insight—Non-Destructive Testing and Condition Monitoring, British Institute of Non-Destructive Testing, GB, vol. 48, No. 1, Jan. 1, 2006 (Jan. 1, 2006), pp. 26-29, XP002459422.

* cited by examiner

DEVICE FOR THE IN-LINE MEASUREMENT OF THE PERCENTAGE OF AUSTENITE IN STEELS

CROSS-REFERENCE TO PRIOR APPLICATIONS

This application is a U.S. National Phase application under 35 U.S.C. § 371 of International Application No. PCT/EP2019/057867, filed on Mar. 28, 2019, and claims benefit to Belgian Patent Application No. BE 2018/5364, filed on Jun. 1, 2018. The International Application was published in French on Dec. 5, 2019 as WO 2019/228692 under PCT Article 21(2).

FIELD

The present invention relates to a magnetic device for measuring, in the production line, the percentage of austenite present in carbon steels and in particular in new AHSS steels (Advanced High Strength Steels) intended mainly for the automobile industry.

BACKGROUND

When carbon steels are produced, it is important to know the fraction of austenite relative to the ferrite matrix at several levels of the manufacturing process.

One example relates to hot rolling. This operation is generally performed at higher temperatures than the ferrite-austenite phase transformation for reasons related to the power required for the rolling mill and also to ensure a stable and known starting point for the microstructure changes that define the final properties of the product.

After the rolling operation, the steels are generally cooled in a controlled manner on an output table. The imposed cooling rates define the final microstructure and the proportions of the different phases (ferrite, bainite, martensite, pearlite) that will constitute the finished product.

To control the cooling rate and thus obtain a final microstructure that is constant over the entire steel strip and therefore controlled mechanical properties, it is of interest to measure the proportion of austenite not yet transformed as a function of time. One may then act on this evolution by modifying the flow rate of the water spray bars and thus change the instantaneous cooling speed.

For this application, magnetic devices are generally used that must be able to operate in the presence of products at high temperature (up to 850° C.) and to react rapidly to variations in microstructure.

In the current state of the art and to the knowledge of the inventors, few devices may be used under these conditions. In addition, these have limitations that make the measurement imprecise or else they are affected by excessive sensitivity to variations in measurement conditions (vibration, change in strip thickness, etc.).

One may cite the PhaseTrack device developed by the ArcelorMittal research center in Maizières, France (reference: for example, tandfonline.com). This device mainly consists of an "E"-shaped metal core. A coil coupled to this core produces a magnetic field in the strip. By measuring the induced magnetic field and by using an appropriate mathematical model, one may deduce the percentage of austenite contained in the strip at the time of measurement. However, this device has two drawbacks. First of all, it is sensitive to the distance between the strip and the sensor itself, which may adversely affect the measurement in the event of vibrations or wear of the support rollers of the strip, for example. Then, the underlying theoretical model must be adapted according to the steel grade to be measured.

The second, more recent device is called EMSpec and was developed by the University of Manchester and the Tata Steel research center in the Netherlands. It is marketed by Primetals (ndt.net). The design of this system makes it largely insensitive to the strip-sensor distance because it is based on the phase of the induced magnetic fields rather than on their amplitude. Nevertheless, the measurement requires to use an alternating current, the frequency of which is varied from 200 Hz to 50 kHz. If one refers to the depths of penetration of such currents in materials of different magnetic permeabilities such as ferrite and austenite, one finds that the measurement is made at widely different depths depending on the phase concerned. The penetration depth may be several millimeters for the austenitic phase but decreases at the highest frequencies to less than 30 µm for the ferrite phase. This may lead to significant errors if the phase proportions are different in the extreme skin and in the mass. This is all the more marked as the grain size of the material is large and approaches the depth of penetration.

Another manufacturing step where measuring the austenite fraction is of great interest is the output of annealing furnaces or galvanizing baths in the context of the production of new strength steels (AHSS). In fact, in these locations, these new steels contain a specific proportion of austenite that will transform into a harder phase (martensite), either during subsequent cooling, or while the material is being shaped at the steel industry customer's. The stability of the mechanical properties of these steels is conditioned by the stability of the austenite proportion at a given point in the process. To control this parameter, it is important that this austenite proportion can be measured.

At the outlet of the galvanizing bath and to the knowledge of the inventors, only the devices described above would be capable of making such measurement. However, in addition to the drawbacks already mentioned, they are not optimized for measurements at this location and in particular the strip-sensor distance must be greater than on an output table for reasons related to possible vibrations of the strip. This reduces the sensitivity of the measurement and vibrations are also unfavorable to the operation of one of these measuring systems.

At the exit of annealing, one may go to lower temperatures at which other devices may operate. This is for example the 3 MA device developed by the Fraunhofer Institute in Germany (gnetworld.com). This system allows to measure 22 magnetic parameters characterizing the properties of the steel. Even if this system is mainly intended for off-line measurements, an implementation on a production line seems possible. However, this system requires complex calibration which must be renewed as soon as the steel grade changes. In addition, it is also sensitive to the strip-sensor distance and to vibrations.

Another device developed by the firm EMG, the IMPOC (emg-automation.com) is specifically designed to make measurements in the production line. The principle consists in generating an induced magnetic field on each face of the strip and in measuring the gradient thus obtained. From correlation laws, the mechanical properties of the sheet may be deduced and, by appropriate calibration, the proportion of austenite too. However, in addition to the fact that the system may only work at temperatures close to ambient temperature, it is also sensitive to the strip-sensor distance, even if the use of average measurements allows to avoid the effect of vibrations.

In document JP H07 190991 A, the aim is to obtain a method and a device allowing to measure the transformation rate of a steel plate whose S/N ratio is improved by eliminating the noise due to the rotation of the rollers by suppressing fluctuations in the density measurement of the magnetic flux created by a magnetic-flux generating means, these fluctuations being generated as a function of a change in ambient temperature, where the transformation-rate measuring device is installed, and as a function of the flow of the time.

The device comprises a housing with magnetization equipment intended to generate a magnetic flux from the lower side of a steel plate, a detection housing comprising a magnetic sensor intended to detect the magnetic flux on the upper side of the steel plate and a signal-processing circuit for obtaining the measured value of the transformation rate from the measurement of the magnetic sensor, the magnetization equipment being installed at a measurement point A and at a reference point B just before a reel on a same production line. Then, with a measurement value at measurement point B as a reference value corresponding to a transformation rate of 100%, an operating circuit is provided for compensating and calculating a measured value of the transformation rate at measurement point A on the basis of the reference value. Documents JP H08 62181 A and JP H07 325067 A describe very similar installations and measurement methods.

Document U.S. Pat. No. 4,740,747 discloses a method and an apparatus for measuring the degree of transformation of the structure of an object. An object is placed between a transmitting coil and a receiving coil. An alternating current or a pulse current or a combination of the alternating current and of the pulse current is supplied to the transmitting coil, and the degree of transformation is detected by means of an electric signal obtained through the receiving coil.

In A. LOIS et al., "Assessment of martensite content in austenic stainless steel specimens by eddy current testing", in Insight—NonDestructive Testing and Condition Monitoring (BINDT), Vol. 48 (1), January 2006, pp. 26-29, an eddy current test (ECT) is applied to estimate the martensite content in an austenitic stainless steel from the impedance modeling (Z) of probes coupled to slightly magnetic materials, and thanks to proper calibration. The voltages measured during the tests were mathematically transformed in the impedance plane and were compared to the theoretical Z curves, showing good correspondence. A linear relationship between the experimental components of Z and the alpha content of the samples was verified, making this procedure suitable for evaluating the martensite content in this type of stainless steels if appropriate calibration parts are available.

SUMMARY

In an embodiment, the present invention provides a method for electromagnetic and real-time measurement of a percentage of austenite contained in a steel strip in continuous motion during in-line manufacture or transformation thereof, by a device comprising the steel strip and a measuring device comprising at least: an alternating-current generator; a first coil supplied by the alternating-current generator, called a transmitting coil, and a second coil, called a receiving coil, the first and second coils being arranged parallel to each other or coaxial and on both sides of the steel strip, a distance between the coils being fixed and between 10 and 200 mm; a core of ferromagnetic material comprising a center of each coil, respectively; at least one voltage-measuring device connected to terminals of the receiving coil, comprising a multimeter or an electronic acquisition system comprising an analog-digital converter coupled to a computer, to obtain the percentage of austenite contained in the steel strip after prior calibration of the device; means of prior calibration for the device so that a magnetic field produced by the alternating current flowing in the transmitting coil produces in the steel strip induced currents that generate an induced magnetic field creating in the receiving coil an electromotive force Vs measurable by the voltage-measuring device, an amplitude of the electromotive force being a function of a voltage Vp applied to the transmitting coil and of a nature of the steel of the strip, the method comprising the following steps: implementing a cooling system for the coils in order to bring the coils to ambient temperature; scrolling the steel strip of unknown austenitic fraction between the coils and measuring the voltage Vs generated at the terminals of the receiving coil for a given voltage Vp applied to the transmitting coil in a voltage range where ratios between the voltages Vs and Vp remain constant if the voltage in the transmitting coil Vp is modified; determining the austenitic fraction of the steel strip as a function of the generated voltage Vs taking into account prior calibration of the device.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1:
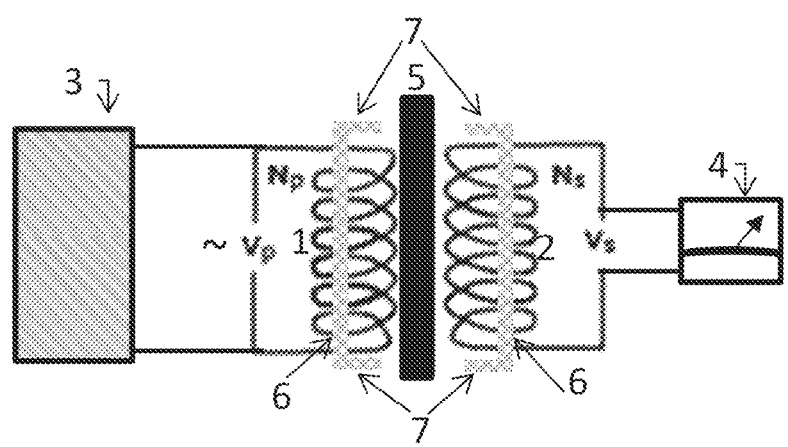
FIG. 1 schematically describes the principle of the device according to the invention.

In an embodiment, the present invention overcomes the limitations of current devices for measuring the austenite fraction in carbon steels in a production line.

In an embodiment, the present invention allows measurement practically in real time both at high and low temperatures of the steel strip.

In an embodiment, the present invention allows measurement at a distance of several tens of millimeters from the strip while maintaining sufficient sensitivity.

In an embodiment, the present invention allows a measurement that is not influenced by the vibrations of the sheet as well as by changes in the strip-sensor distance, which may be relatively large.

Finally, the device according to the invention must be simple, inexpensive and operate above and below the Curie point.

The device of the invention is characterized by two coils made of electrically-conductive wire, for example copper, wound around a ferromagnetic core.

The first coil, called the transmitting coil, is connected to an alternating-current generator, the second coil, called the receiving coil, is connected to a device which allows to measure the alternating voltage generated at its terminals, for example a voltmeter but also any other device such as an acquisition, recording and/or display system.

According to the invention, the two coils are arranged on both sides of the steel strip at a fixed distance between them, the distance between the strip and each of the coils may however vary as a result, for example, of the vibrations of the strip.

More specifically, a first aspect of the present invention relates to a method for the electromagnetic and real-time measurement of the percentage of austenite contained in a steel strip in continuous motion during an in-line manufacture or transformation thereof, by means of a device consisting of said steel strip and of a measuring device comprising at least:
- an alternating-current generator;
- a first coil supplied by the alternating-current generator, called the transmitting coil, and a second coil, called the receiving coil, the first and second coils being arranged parallel to each other or coaxial and on both sides of the steel strip, the distance between the coils being fixed and comprised between 10 and 200 mm;
- a core of ferromagnetic material constituting the center of each coil, respectively;
- at least one voltage-measuring device connected to the terminals of the receiving coil, in the form of a multimeter or of an electronic acquisition system comprising an analog-digital converter coupled to a computer, to obtain the percentage of austenite contained in the steel strip after prior calibration of the device;
- means of prior calibration for the device;

so that the magnetic field produced by the alternating current flowing in the transmitting coil produces in the steel strip induced currents, that generate an induced magnetic field creating, in the receiving coil, an electromotive force Vs that can be measured by the voltage-measuring device, the amplitude of this electromotive force being a function of the voltage Vp applied to the transmitting coil and of the nature of the steel of the strip;

said method being characterized at least by the following steps:
- a cooling system is implemented for the coils in order to bring them to ambient temperature;
- a steel strip of unknown austenitic fraction is scrolled between the coils and the voltage Vs generated at the terminals of the receiving coil is measured for a given voltage Vp applied to the transmitting coil in a voltage range where the ratios between the voltages Vs and Vp remain constant if the voltage in the transmitting coil Vp is modified;
- taking into account prior calibration of the device, the austenitic fraction of the steel strip is determined as a function of the generated voltage Vs.

According to preferred embodiments of the invention, the method is further limited by one of the following characteristics or by an appropriate combination of them:
- the prior calibration of the device is carried out by scrolling, between the two coils, strips of different grades of steel and of known austenitic fraction, and by measuring the voltage generated at the terminals of the receiving coil, for each voltage value at the transmitting coil within a certain range;
- the proportion of austenite in the steel strip is controlled during the in-line manufacture or transformation method thereof, so as to ensure the stability of the austenic phase and consequently the stability of the mechanical properties of the steel before subsequent transformation into harder finishing phases;
- in the device used, the core of ferromagnetic material comprises at least one thin flat plate that is parallel to the surface of the steel strip;
- in the device used, the core of ferromagnetic material comprises at least one cylinder with an axis that is parallel or perpendicular to the surface of the steel strip;
- in the device used, the two coils are of the same size and are placed symmetrically with respect to the steel strip;
- in the device used, the frequency of the alternating-current generator is between 50 and 500 Hz;
- in the device used, the frequency of the alternating-current generator is between 50 and 60 Hz;
- in the device used, the core of ferromagnetic material comprises at least one main plate or a cylinder and a bar or a secondary plate that is perpendicular to the main plate or to the cylinder at each end thereof, to bend the field lines that will be generated or picked up by the respective coils;
- in the device used, the axis of the coils is perpendicular to the motion direction of the strip;
- in the device used, the fixed distance between the coils is comprised between 10 and 20 mm;
- in the device used, each coil comprises from 100 to 500 turns of electric wire that is suitable for letting an alternating current comprised between 2 and 5 A;
- in the device used, the number of turns is 5 to 10 times greater in the receiving coil than in the transmitting coil;
- in the device used, the strip size or section covered by the thin plate or cylinder is of the order of 100×100 mm to 200×200 mm;
- the device used comprises a water or air cooling system to maintain the coils at a temperature close to ambient temperature, preferably in a regulated manner.

A second aspect of the present invention relates to a use of the aforementioned method in a hot-rolling mill, in the case of a steel strip at a temperature that is below the Curie temperature, the austenitic fraction of the steel strip being determined by using fluctuations in magnetic permeability.

A third aspect of the present invention relates to a use of the aforementioned method in a hot-rolling mill, in the case of a steel strip at a temperature that is above the Curie temperature, the austenitic fraction of the steel strip being determined by using eddy current fluctuations linked to the difference in resistivity between austenite and ferrite.

The invention relates to a magnetic device allowing to measure the proportion of austenite in a carbon steel. This invention aims essentially, but not exclusively, at two applications in the production of steels:
- the control of cooling on the hot-rolling output table where knowing the austenite percentage allows to control cooling rates;
- the control of the mechanical properties of AHSS steels at the output of annealing lines and galvanizing baths.

In these two cases, controlling the proportion of austenite allows to ensure the stability of the mechanical properties by ensuring the stability of the austenitic phase which must turn into harder phases at the end of the in-line cooling or when the steel is deformed at the customer's premises.

The device mainly comprises two coils, each of them manufactured by winding an electrical conductor wire on a ferromagnetic core. This core generally consists of a plate, which may be flat or bent, a few millimeters thick and possibly terminated at each end by a bar or another plate that is perpendicular to the main plate. These ends, which are not essential to the invention, are intended to bend the lines of the magnetic field that will be generated or picked up by the coils.

The dimensions of the main plate of the core may vary to a large extent depending on whether an average value of the austenite percentage should be obtained over the entire width of the steel strip or more locally in order to possibly establish a distribution profile of the austenitic fraction over the width of the strip.

The plates are preferably placed parallel to the surface of the sheet, one on each side, facing each other, and the wire is preferably wound in the width direction of the steel strip, although any other configuration may be considered. For example, the plates could advantageously be replaced by cylinders with an axis placed either parallel or perpendicular to the surface of the steel strip, one on each side thereof.

A current generator passes an alternating current through the first coil. This current, that may vary over time, generates a variable magnetic field in the steel strip with the creation of induced currents, the eddy currents. Depending on the more or less ferromagnetic and more or less resistive nature of this strip, these eddy currents create a more or less significant induced magnetic field which passes through and is picked up by the second coil (receiving coil). This field generates, at the terminals of this coil, an alternating voltage (electromotive force) whose amplitude depends on the nature of the material constituting the steel strip. This voltage may be measured or recorded using a device such as a voltmeter or any other acquisition or measurement system, the principle of which is known to those skilled in the art.

By simple and direct calibration, it is then easy to relate the measured voltage to the percentage of austenite present in the steel strip.

The inductance of the receiving coil is conditioned by the sensitivity of the measuring device. It is thus possible to use, for example, a hundred turns for the first coil and a current of a few amps while using a number of turns five to ten times greater for the secondary coil.

The frequency of the alternating current is ideally low enough to avoid the skin effect and to allow an analysis in the greatest possible thickness of the sheet. A frequency of 50 to 60 Hz is particularly interesting since it corresponds to that of electrical energy distribution networks.

A lower frequency is not recommended because the reaction time to stabilize the measurement would become too large for the production speeds of the industrial lines mainly targeted by the invention.

Conversely, a higher frequency, up to approximately 500 Hz, may be used to keep a reduced but sufficient depth of penetration of the induced currents.

This device is particularly simple and may be made of materials that are resistant to temperature. A water or air cooling system for example allows it to be used in places where the strip to be measured is at high temperature.

In addition, as the intensity of magnetic induction varies linearly with distance, only the distance between the two coils needs to be constant and not the distance between any of the coils and the sheet. This allows to overcome vibrations or changes in the position of the strip to be measured.

As a result, the present invention avoids most of the drawbacks of the measurement systems described in the prior art.

Figure 2:
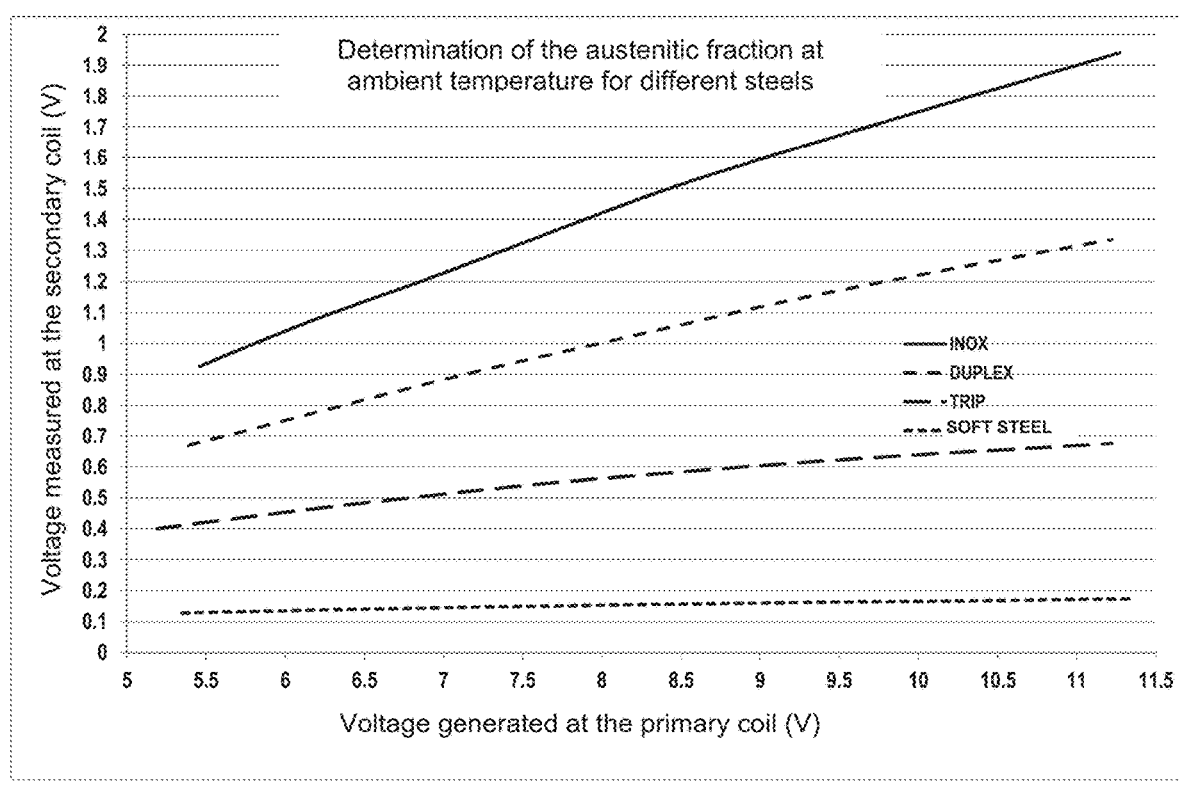
FIG. 2 illustrates the evolution, at ambient temperature, of the voltage at the terminals of the receiving coil as a function of the voltage applied to the terminals of the transmitting coil for various types of steels containing different fractions of austenite.

FIG. 2 illustrates the sensitivity of the measurement at ambient temperature on four types of steel that contain different austenite percentages, from a purely ferritic steel ("mild steel") to a purely austenitic steel ("stainless steel"). "TRIP" and "Duplex" steels contain approximately 15-20% and 60% austenite, respectively. By applying voltage to the transmitting coil (abscissa), a voltage is generated in the receiving coil (ordinate) that depends on the austenite percentage in the steel. In addition, as may be seen in this figure, the ratios between the voltages remain practically constant if the voltage in the transmitting coil is modified.

In document JP H07 190991 A, the detection system is intended for the output tables of hot-rolling mills and to be used according to phase changes that occur at temperatures below the Curie temperature because it is exclusively based on the correlation between the variations in magnetic permeability and the mechanical characteristics of the steel strip.

In the present application, the detection system may also be used above the Curie point because the signal processing comprises the variations due to the eddy currents linked to the different resistivity of the austenitic and ferritic phases. This property is interesting because if there are steels in a 100% austenitic phase whose temperature is lower than the Curie temperature (eutectoid steels for example), the phase transformation occurs above the Curie temperature for most steels and in particular the new AHSS steels.

The device proposed according to a preferred embodiment of the invention is schematically described in FIG. 1. The two coils 1, 2 are placed on both sides of the strip to be analyzed at a distance that is preferably comprised between 10 and 20 mm. The plates constituting the core of the coils each comprise a main plate 6 and a bar or a secondary plate 7 located perpendicular to the ends of the main plate 6. The size of the plates of ferromagnetic material constituting the core of the coils varies ideally, but not exclusively, with a covered strip section or area of the order of 100 mm×100 mm up to 200 mm×200 mm depending on the width over which the signal should be averaged. Their thickness is ideally comprised between 2 and 5 mm.

Each coil consists of 100 to 500 turns of a wire having sufficient diameter to pass an alternating current of the order of 2 to 5 amperes obtained for example using a rheostat autotransformer 3 connected to the network. The voltage at the secondary is measured using a multimeter 4.

In another preferred embodiment, the autotransformer is replaced by an alternating-current generator having a frequency comprised between 100 and 500 Hz, which allows to keep sufficient depth of penetration for the analysis of thin sheets (1 to 2 mm thick) while allowing to react more quickly to local variations in the austenite percentage.

Another preferred embodiment further comprises a cooling circuit, ideally with water or with another heat-transfer fluid. The latter maintains the temperature of the coils at a value close to ambient temperature, preferably in a controlled manner. This embodiment allows to carry out measurements on a steel strip heated to high temperature without uncontrollably increasing the resistivity of the wire of the coils.

In yet another preferred embodiment, the multimeter is replaced by an electronic acquisition system consisting of an analog-digital converter connected to a computer that records and displays the measured values. This computer may also convert the measured voltage into a percentage of austenite thanks to the use of pre-established calibration data.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for electromagnetic and real-time measurement of a percentage of austenite contained in a steel strip in continuous motion during in-line manufacture or transformation thereof, by a device comprising the steel strip and a measuring device comprising at least: an alternating-current generator; a first coil supplied by the alternating-current generator, called a transmitting coil, and a second coil, called a receiving coil, the first and second coils being arranged parallel to each other or coaxial and on both sides of the steel strip, a distance between the coils being fixed and between 10 mm and 200 mm; a core of ferromagnetic material comprising a center of each coil, respectively; at least one voltage-measuring device connected to terminals of the receiving coil, comprising a multimeter or an electronic acquisition system comprising an analog-digital converter coupled to a computer, to obtain the percentage of austenite contained in the steel strip after prior calibration of the device; means of prior calibration for the device so that a magnetic field produced by the alternating current flowing in the transmitting coil produces in the steel strip induced currents that generate an induced magnetic field creating in the receiving coil an electromotive force Vs measurable by the voltage-measuring device, an amplitude of the electromotive force being a function of a voltage Vp applied to the transmitting coil and of a nature of the steel of the strip, the method comprising the following steps:
   implementing a cooling system for the coils in order to bring the coils to ambient temperature;
   scrolling the steel strip of unknown austenitic fraction between the coils and measuring the voltage Vs generated at the terminals of the receiving coil for a given voltage Vp applied to the transmitting coil in a voltage range where ratios between the voltages Vs and Vp remain constant if the voltage in the transmitting coil Vp is modified; and
   determining the austenitic fraction of the steel strip as a function of the generated voltage Vs taking into account prior calibration of the device.

2. The method according to claim 1, wherein the prior calibration of the device is carried out by scrolling, between the two coils, strips of different grades of steel and of known austenitic fraction, and by measuring a voltage generated at the terminals of the receiving coil, for each voltage value at the transmitting coil.

3. The method according to claim 1, wherein a proportion of austenite in the steel strip is controlled during the in-line manufacture or transformation method thereof, so as to ensure stability of an austenitic phase and consequently stability of mechanical properties of a steel of the steel strip before subsequent transformation into harder finishing phases.

4. The method according to claim 1, wherein, in the device used, the core of ferromagnetic material comprises at least one thin flat plate that is parallel to a surface of the steel strip.

5. The method according to claim 1, wherein, in the device used, the core of ferromagnetic material comprises at least one cylinder with an axis that is parallel or perpendicular to a surface of the steel strip.

6. The method according to claim 1, wherein, in the device used, the two coils are of a same size and placed symmetrically with respect to the steel strip.

7. The method according to claim 1, wherein, in the device used, a frequency of the alternating-current generator is between 50 Hz and 500 Hz.

8. The method according to claim 1, wherein, in the device used, the frequency of the alternating-current generator is between 50 Hz and 60 Hz.

9. The method according to claim 4, wherein, in the device used, the core of ferromagnetic material comprises at least one main plate or a cylinder, and a bar or a secondary plate that is perpendicular to the main plate or cylinder at each end thereof, to bend field lines generated or picked up by the respective coils.

10. The method according to claim 1, wherein, in the device used, an axis of the coils is perpendicular to a direction of the steel strip.

11. The method according to claim 1, wherein, in the device used, the fixed distance between the coils is between 10 mm and 20 mm.

12. The method according to claim 1, wherein in the device used, each coil comprises from 100 turns to 500 turns of electric wire.

13. The method according to claim 12, wherein, in the device used, a number of turns is 5 times to 10 times greater in the receiving coil than in the transmitting coil.

14. The method according to claim 9, wherein, in the device used, a strip size or section covered by the at least one main plate or by the cylinder is of an order of 100 mm×100 mm to 200 mm×200 mm.

15. The method according to claim 1, wherein the alternating-current generator comprises a rheostat autotransformer.

16. The method according to claim 1, wherein the device used comprises a water or air cooling system to maintain the coils at a temperature that is close to ambient temperature.

17. The method according to claim 1, wherein the method is used in a hot-rolling mill,
   wherein the temperature of the steel strip is below the Curie temperature, and
   wherein the determining the austenitic fraction of the steel strip comprises using fluctuations in magnetic permeability.

18. The method according to claim 1, wherein the method is used in a hot-rolling mill,
   wherein the temperature of the steel strip is above the Curie temperature, and wherein the determining the austenitic fraction of the steel strip comprises using eddy current fluctuations linked to a difference in resistivity between austenite and ferrite.

19. The method according to claim 16, wherein the water or air cooling system maintains the coils at the temperature that is close to ambient temperature in a regulated manner.

* * * * *